United States Patent
Chung et al.

(10) Patent No.: US 10,307,132 B2
(45) Date of Patent: Jun. 4, 2019

(54) STETHOSCOPE HEAD AND STETHOSCOPE COMPRISING SAME

(71) Applicant: SAMSUNG ELECTRONICS CO., LTD., Suwon-si (KR)

(72) Inventors: Hae-In Chung, Anyang-si (KR); Young-hwan Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 56 days.

(21) Appl. No.: 15/511,124

(22) PCT Filed: Dec. 18, 2014

(86) PCT No.: PCT/KR2014/012511
§ 371 (c)(1),
(2) Date: Mar. 14, 2017

(87) PCT Pub. No.: WO2016/043385
PCT Pub. Date: Mar. 24, 2016

(65) Prior Publication Data
US 2017/0251997 A1  Sep. 7, 2017

(30) Foreign Application Priority Data

Sep. 15, 2014 (KR) .......................... 10-2014-0122033

(51) Int. Cl.
*A61B 5/04* (2006.01)
*A61B 7/04* (2006.01)
(Continued)

(52) U.S. Cl.
CPC .............. *A61B 7/04* (2013.01); *A61B 5/0408* (2013.01); *A61B 5/04085* (2013.01); *A61B 7/00* (2013.01);
(Continued)

(58) Field of Classification Search
CPC .................. A61B 7/04; A61B 5/04085; A61B 2562/0204; A61B 2560/0242; A61L 2/10; A61L 2/24; A61L 2202/14
See application file for complete search history.

(56) References Cited

U.S. PATENT DOCUMENTS 4,007,806 A * 2/1977 Nobles, Jr. ............... A61B 7/02
181/131
6,757,392 B1 6/2004 Granzotto et al.
(Continued)

FOREIGN PATENT DOCUMENTS

CN 203139162 U 8/2013
EP 2 582 401 A1 12/2012
(Continued)

OTHER PUBLICATIONS

Written Opinion dated May 29, 2015 issued by International Searching Authority in counterpart International Application No. PCT/KR2014/012511 (PCT/ISA/237).
(Continued)

*Primary Examiner* — Christopher Koharski
*Assistant Examiner* — Natasha Patel
(74) *Attorney, Agent, or Firm* — Sughrue Mion, PLLC

(57) ABSTRACT

A stethoscope head, according to an embodiment of the present invention, may include: an auscultatory sound receiver; a support member configured to support the auscultatory sound receiver; and a moving member comprising a light source configured to emit ultraviolet rays for sterilization to the auscultatory sound receiver, and capable of moving a position thereof with respect to the auscultatory sound receiver and the support member in a first direction orienting to an object and a second direction opposite to the first direction.

19 Claims, 15 Drawing Sheets

(51) Int. Cl.
*A61B 5/0408* (2006.01)
*A61L 2/10* (2006.01)
*A61L 2/24* (2006.01)
*A61B 7/00* (2006.01)

(52) U.S. Cl.
CPC ............... *A61L 2/10* (2013.01); *A61L 2/24* (2013.01); *A61B 2560/0242* (2013.01); *A61B 2562/0204* (2013.01); *A61L 2202/14* (2013.01)

(56) References Cited

U.S. PATENT DOCUMENTS

| | | | |
|---|---|---|---|
| 7,082,202 | B1 | 7/2006 | Orten |
| 7,806,226 | B2 | 10/2010 | Drummond et al. |
| 9,345,451 | B2 | 5/2016 | Lee et al. |
| 9,387,268 | B2 | 7/2016 | Farren |
| 2004/0260193 | A1 | 12/2004 | LaSala |
| 2005/0048455 | A1* | 3/2005 | Hayamizu ............ G09B 23/288 434/262 |
| 2006/0227979 | A1* | 10/2006 | Chen ...................... A61B 7/04 381/67 |
| 2008/0232604 | A1 | 9/2008 | Dufresne et al. |
| 2009/0212234 | A1* | 8/2009 | Vestal ..................... A61L 2/10 250/455.11 |
| 2012/0093520 | A1 | 4/2012 | Draaijer et al. |
| 2015/0297105 | A1* | 10/2015 | Pahlevan ........... A61B 5/02427 600/301 |

FOREIGN PATENT DOCUMENTS

| | | |
|---|---|---|
| EP | 2762169 A1 | 8/2014 |
| JP | 2002-532127 A | 10/2002 |
| JP | 2005-227534 A | 8/2005 |
| JP | 2012-55354 A | 3/2012 |
| KR | 1999-028685 A | 4/1999 |
| KR | 10-2005-0035952 A | 4/2005 |
| KR | 10-2006-0113085 A | 11/2006 |
| KR | 10-2008-0022354 A | 3/2008 |
| KR | 10-2008-0028393 A | 3/2008 |
| KR | 10-2012-0003907 A | 1/2012 |
| KR | 10-1303611 B1 | 9/2013 |
| KR | 10-1324463 B1 | 10/2013 |
| KR | 10-2014-0045189 A | 4/2014 |

OTHER PUBLICATIONS

International Search Report dated May 29, 2015 issued by International Searching Authority in counterpart PCT/KR2014/012511 (PCT/ISA/210).

Communication dated Sep. 7, 2015 issued by Korean Intellectual Property Office in counterpart Korean Application No. 10-2014-0122033.

Communication dated Oct. 11, 2017, issued by the European Patent Office in counterpart European Application No. 14901870.7.

* cited by examiner

STETHOSCOPE HEAD AND STETHOSCOPE COMPRISING SAME

TECHNICAL FIELD

Embodiments relate to a stethoscope head and a stethoscope apparatus including the same.

BACKGROUND ART

A stethoscope apparatus is used to check whether a status of a patient is normal by listening to a cardiac sound, a respiratory sound, an artery sound, intestine noise, and a vascular sound occurring in a human body. The stethoscope apparatus includes an auscultatory sound receiver, e.g., a diaphragm, for receiving an auscultatory sound from a patient by being in contact with a portion of the body of the patient.

The diaphragm may be easily contaminated by various kinds of viruses or bacteria during a process of being in contact with a plurality of patients and a process of being exposed to the outside for a long time.

In addition, when a temperature of the diaphragm is lower than a body temperature of a patient, the patient may have an unpleasant feeling due to the temperature difference between the diaphragm and the patient when the patient is in contact with the diaphragm.

To solve such a contamination of a diaphragm and such an unpleasant feeling of a patient, a sterilization device for sterilizing a diaphragm and a pre-heating device for pre-heating a diaphragm have been developed. However, since the sterilization device and the pre-heating device are configured separately from a stethoscope apparatus, it is cumbersome that a user should attach these devices to the stethoscope apparatus every time sterilization and pre-heating are necessary. In addition, it is cumbersome that the sterilization device and the pre-heating device should be detached from the stethoscope apparatus when sterilization and pre-heating are not necessary.

DETAILED DESCRIPTION OF THE INVENTION

Technical Problem

Provided are a stethoscope head capable of pre-heating and sterilizing by itself without attaching a separate device thereto and a stethoscope apparatus including the same.

Provided are a stethoscope head capable of pre-heating and sterilizing without a separate behavior of a user and a stethoscope apparatus including the same.

Provided are a stethoscope head which is easy to carry and enables accurate electrocardiogram measurement and a stethoscope apparatus including the same.

Provided is a stethoscope apparatus capable of effectively removing noise due to friction between a stethoscope head and an object by measuring a pressure of the stethoscope head on the object with a simple structure.

Technical Solution

According to an aspect of an embodiment, a stethoscope head includes: an auscultatory sound receiver configured to receive an auscultatory sound from an object; a support member configured to support at least a part of a circumferential region of the auscultatory sound receiver; and a moving member including a light source configured to emit ultraviolet rays for sterilization to the auscultatory sound receiver, and capable of moving a position thereof with respect to the auscultatory sound receiver and the support member in a first direction orienting to the object and a second direction opposite to the first direction.

When the stethoscope head is in contact with the object, the moving member may move in the second direction, and when the stethoscope head is away from the object, the moving member may move in the first direction.

The moving member may have a first position at which the light source protrudes in the first direction than the auscultatory sound receiver and a second position which is apart in the second direction from the first position.

When the moving member is located at the first position, the light source may emit ultraviolet rays on the front surface of the auscultatory sound receiver, which faces the object.

The light source may be disposed such that a center direction of the emission of the ultraviolet rays makes an acute angle with the auscultatory sound receiver.

The moving member may further include a heating source configured to heat the auscultatory sound receiver.

When the moving member is located at the first position, the heating source may be in contact with the auscultatory sound receiver.

When the moving member is located at the second position, the heating source may be away from the auscultatory sound receiver.

The heating source may be equipped with the light source and include a thermal conductive member.

The moving member may further include a temperature sensor configured to measure a temperature of the heating source.

The stethoscope head may further include a contact sensor configured to be pressed according to movement of the moving member.

When the moving member moves in the second direction, the contact sensor may be pressed, and the light source may stop emitting the ultraviolet rays.

The stethoscope head may further include a proximity sensor configured to detect an approach of an external object to the light source.

The stethoscope head may further include a plurality of electrocardiogram (ECG) electrodes configured to measure an ECG of the object, wherein at least one of the plurality of ECG electrodes is movable.

The plurality of ECG electrodes may have a measurement position at which an ECG is measured from the object and a standby position at which the ECG is not measured from the object.

Separation distances between the plurality of ECG electrodes when the plurality of ECG electrodes are located at the measurement position may be greater than separation distances between the plurality of ECG electrodes when the plurality of ECG electrodes are located at the standby position.

According to an aspect of another embodiment, a stethoscope apparatus includes: the stethoscope head; and a handle connected to the stethoscope head.

The handle may be rotatably connected to the stethoscope head.

The stethoscope apparatus may further include a pressure detector configured to detect pressure of the handle on the stethoscope head.

At least one of the stethoscope head and the handle may further include an output part configured to provide information to a user.

According to an aspect of another embodiment, a stethoscope head includes: an auscultatory sound receiver configured to receive an auscultatory sound from an object; a support member configured to support at least a part of a circumferential region of the auscultatory sound receiver; and a moving member including a heating source configured to heat the auscultatory sound receiver, and capable of moving a position thereof with respect to the auscultatory sound receiver and the support member in a first direction orienting to the object and a second direction opposite to the first direction.

According to an aspect of another embodiment, a stethoscope apparatus includes: a stethoscope head including an auscultatory sound receiver configured to receive an auscultatory sound from an object; a handle movably connected to the stethoscope head; and a pressure detector configured to detect a pressure of the handle on the stethoscope head.

According to an aspect of another embodiment, a stethoscope apparatus includes: a stethoscope head including an auscultatory sound receiver configured to receive an auscultatory sound from an object; and a plurality of electrocardiogram (ECG) electrodes disposed on the stethoscope head and configured to measure an ECG of the object, wherein at least one of the plurality of ECG electrodes is movable.

Advantageous Effects of the Invention

According to embodiments, in a stethoscope head and a stethoscope apparatus including the same, since a light source for emitting ultraviolet rays on an auscultatory sound receiver of the stethoscope head is movable back and forth with respect to the auscultatory sound receiver and a support member supporting the auscultatory sound receiver, pre-heating and sterilization may be performed without attaching a separate device. In addition, since pre-heating and sterilization are determined by a behavior occurring during a stethoscope process, the pre-heating and the sterilization may be performed without a user's additional behavior.

According to another embodiment, in a stethoscope head and a stethoscope apparatus including the same, since positions of some of electrocardiogram (ECG) electrodes for measuring an ECG are movable, it is easy to carry the stethoscope apparatus, and an ECG may be accurately measured.

According to another embodiment, a stethoscope apparatus may effectively remove noise due to friction between a stethoscope head and an object by detecting a pressure of the stethoscope head on the object through a pressure detector.

MODE OF THE INVENTION

Figure 1:
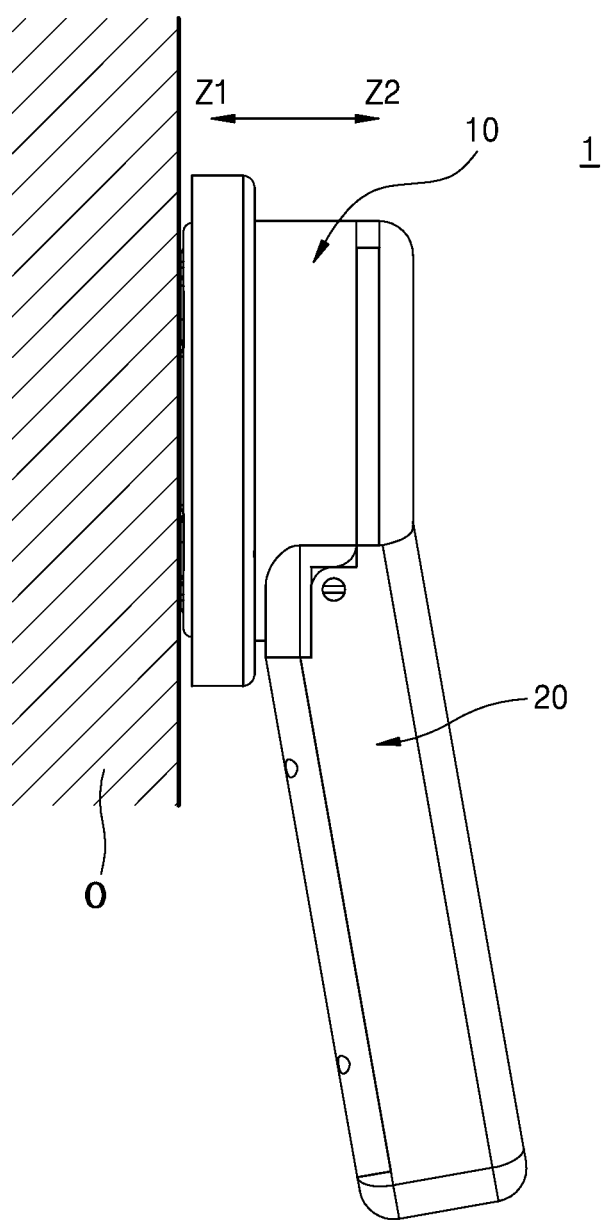
FIG. 1 is a side view for describing a stethoscope apparatus including a stethoscope head according to an embodiment of the present invention.

The terms used in the present invention are those general terms currently widely used in the art while taking into account functions in the present invention, but the terms may vary according to the intention of those of ordinary skill in the art, precedents, or new technology in the art. Also, specified terms may be selected by the applicant, and in this case, the detailed meaning thereof will be described in the detailed description. Thus, the terms used in the present invention should be understood not as simple names but based on the meaning of the terms and the overall invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

In the present specification, the term "object" may include a human being, a creature, or a portion of the human being or the creature.

In the present specification, the term "user" may be a medical practitioner or a nurse as a medical expert but is not limited thereto. For example, the user may be the object or a third party other than the object or the user.

Hereinafter, embodiments of the present invention will be described in detail with reference to the accompanying drawings so that those of ordinary skill in the art may easily realize the present invention. However, the present invention may be embodied in many different forms and should not be construed as being limited to the embodiments set forth herein. In the drawings, parts irrelevant to the description are omitted to clearly describe the present invention, and like reference numerals denote like elements throughout the specification.

FIG. 1 is a side view for describing a stethoscope apparatus 1 including a stethoscope head 10 according to an embodiment of the present invention. Referring to FIG. 1, the stethoscope apparatus 1 includes the stethoscope head 10. The stethoscope apparatus 1 may be a digital electronic stethoscope apparatus but is not limited thereto. For example, the stethoscope apparatus 1 may be an analog stethoscope apparatus.

The stethoscope head 10 is a part to be in contact with an object O and receives an auscultatory sound from the object O in contact therewith. Information about the received auscultatory sound is provided to a user or a third party through an output part (not shown). Herein, a direction orienting from the stethoscope head 10 to the object O is defined as a first direction Z1, and an opposite direction to the first direction Z1 is defined as a second direction Z2.

The stethoscope head 10 may be connected to a handle 20 which is a part for the user to grip the stethoscope head 10.

Figure 2:
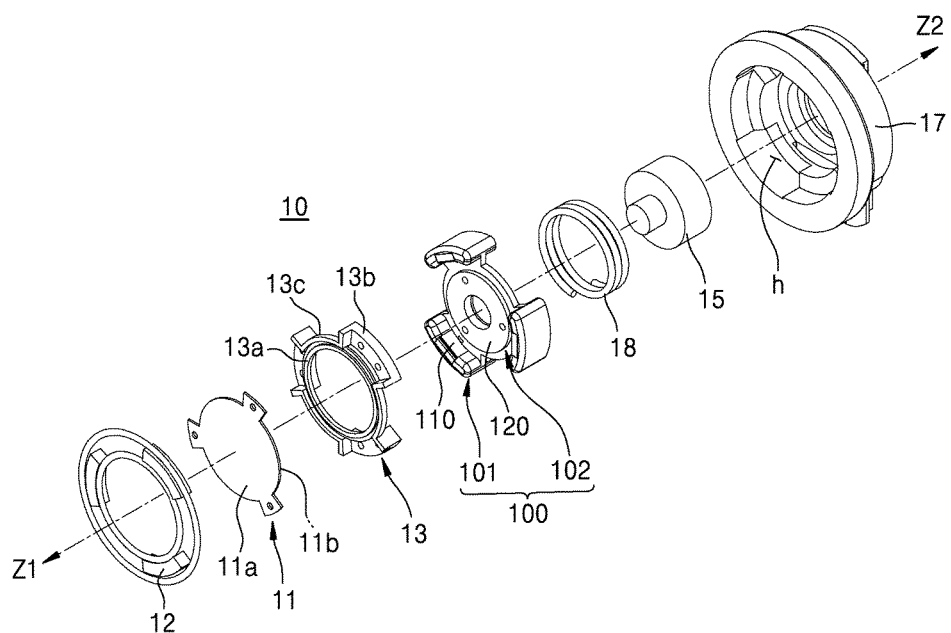
FIG. 2 is an exploded perspective view of the stethoscope head shown in FIG. 1.

FIG. 2 is an exploded perspective view of the stethoscope head 10 shown in FIG. 1. Referring to FIG. 2, the stethoscope head 10 may include an auscultatory sound receiver 11, a support member 13, a microphone 15, and a head case 17.

The auscultatory sound receiver 11 is to receive an auscultatory sound from the object O and includes a front surface 11a orienting the object O and a rear surface 11b located in an opposite direction to the front surface 11a. The auscultatory sound receiver 11 may be a diaphragm capable of vibrating according to a change in the object O.

The auscultatory sound receiver 11 may receive an auscultatory sound by vibrating according to a change in the object O in a state of being in contact with the object O. The change in the object O may be various, for example, vibrations of a surface of the object O due to heartbeats of the object O.

The auscultatory sound receiver 11 may further include an elastic contact part 12. The elastic contact part 12 is in elastic contact with the object O and presses and supports an outer side of a contact region of the object O in contact with the auscultatory sound receiver 11. Accordingly, noise of an auscultatory sound received by the auscultatory sound receiver 11 may be reduced.

The support member 13 supports at least a part of a circumferential region of the auscultatory sound receiver 11. The auscultatory sound receiver 11 has the circumferential region of which at least a part is fixed by the support member 13, and a center region located at an inner side of the circumferential region may vibrate.

The support member 13 includes a support region 13a, which supports the auscultatory sound receiver 11, and a plurality of protrusion regions 13b protruding in a radius direction from the support region 13a. The plurality of protrusion regions 13b are supported by the head case 17, and grooves 13c may be formed between the protrusion regions 13b.

The microphone 15 converts an auscultatory sound received through the auscultatory sound receiver 11 into an electrical signal. For example, the microphone 15 may include a piezoelectric transducer. The microphone 15 may be disposed so as to be in contact with the rear surface 11b of the auscultatory sound receiver 11. Accordingly, when the auscultatory sound receiver 11 vibrates, a pressure applied to the microphone 15 in contact with the rear surface 11b of the auscultatory sound receiver 11 varies, and the microphone 15 may convert this pressure change into an electrical signal. The electrical signal converted by the microphone 15 may be amplified by an amplifier (not shown) and delivered to the user. According to this structure in which the microphone 15 is in contact with the auscultatory sound receiver 11, an influence due to noise may be reduced than a structure in which the microphone 15 is separated from the auscultatory sound receiver 11.

However, the microphone 15 is not limited to the structure including the piezoelectric transducer. As another example, the microphone 15 may include a capacitive transducer.

The head case 17 supports the support member 13 and the microphone 15. The head case 17 forms an outer appearance of the stethoscope head 10 and protects the support member 13 and the microphone 15 from the outside. The head case 17 includes an opening h to which the auscultatory sound receiver 11 and the support member 13 are coupled.

The auscultatory sound receiver 11 of the stethoscope head 10 is a part being in contact with the object O during auscultation and exposed to the outside when the auscultatory process is not performed. Accordingly, the auscultatory sound receiver 11 may be easily contaminated from viruses (or bacteria). In addition, if a temperature of the auscultatory sound receiver 11 differs from a temperature of the object O, the object O may have an unpleasant feeling due to this temperature difference when the auscultatory sound receiver 11 is in contact with the object O for auscultation.

The stethoscope head 10 according to the present embodiment may further include a moving member 100 including a light source 110 and a heating source 120 for sterilization and pre-heating of the auscultatory sound receiver 11.

The light source 110 may emit ultraviolet rays on the auscultatory sound receiver 11. The light source 110 may sterilize (or disinfect) the auscultatory sound receiver 11 by emitting ultraviolet rays on the auscultatory sound receiver 11, thereby removing viruses existing on the auscultatory sound receiver 11.

The heating source 120 may heat the auscultatory sound receiver 11. The heating source 120 may be in contact with the auscultatory sound receiver 11 and conductively heat the auscultatory sound receiver 11. The heating source 120 may heat the auscultatory sound receiver 11 at a predetermined temperature. For example, the heating source 120 may heat the auscultatory sound receiver 11 such that the auscultatory sound receiver 11 becomes a temperature similar to that of the object O. The temperature similar to that of the object O may be, for example, 34° to 40°.

The heating source 120 may heat the auscultatory sound receiver 11 before auscultation. Pre-heating of the auscultatory sound receiver 11 by using the heating source 120 may remove or minimize an unpleasant feeling which the object O may have due to a temperature difference between the auscultatory sound receiver 11 and the object O when the auscultatory sound receiver 11 is in contact with the object O for auscultation.

The moving member 100 including the light source 110 and the heating source 120 can move a position thereof in the first direction Z1 and the second direction Z2 with respect to the auscultatory sound receiver 11 and the support member 13.

The moving member 100 may include the contact region 102, which may be in contact with the rear surface 11b of the auscultatory sound receiver 11, and a plurality of protrusion regions 101 protruding in the first direction Z1 from the contact region 102. At least a part of the heating source 120 may be included in the contact region 102, and the light source 110 may be included in the protrusion regions 101. The protrusion regions 101 of the moving member 100 are inserted into the grooves 13c formed in the support member 13, and at least a part of the protrusion regions 101 may protrude in the first direction Z1 than the auscultatory sound receiver 11. Accordingly, when the stethoscope head 10 is in contact with the object O, the protrusion regions 101 may be pressed in the second direction Z2 by the object O.

An elastic member 18 may be disposed between the moving member 100 and the head case 17. For example, the elastic member 18 may be disposed between the rear surface of the contact region 102 of the moving member 100 and an inner surface of the head case 17. The moving member 100 may be pressed in the first direction Z1 by the elastic member 18. The elastic member 18 may be a coil spring of a metal material but is not limited thereto. For example, the elastic member 18 may be another type of spring or be of another material, for example, a rubber material having elasticity by itself.

Figure 3A:
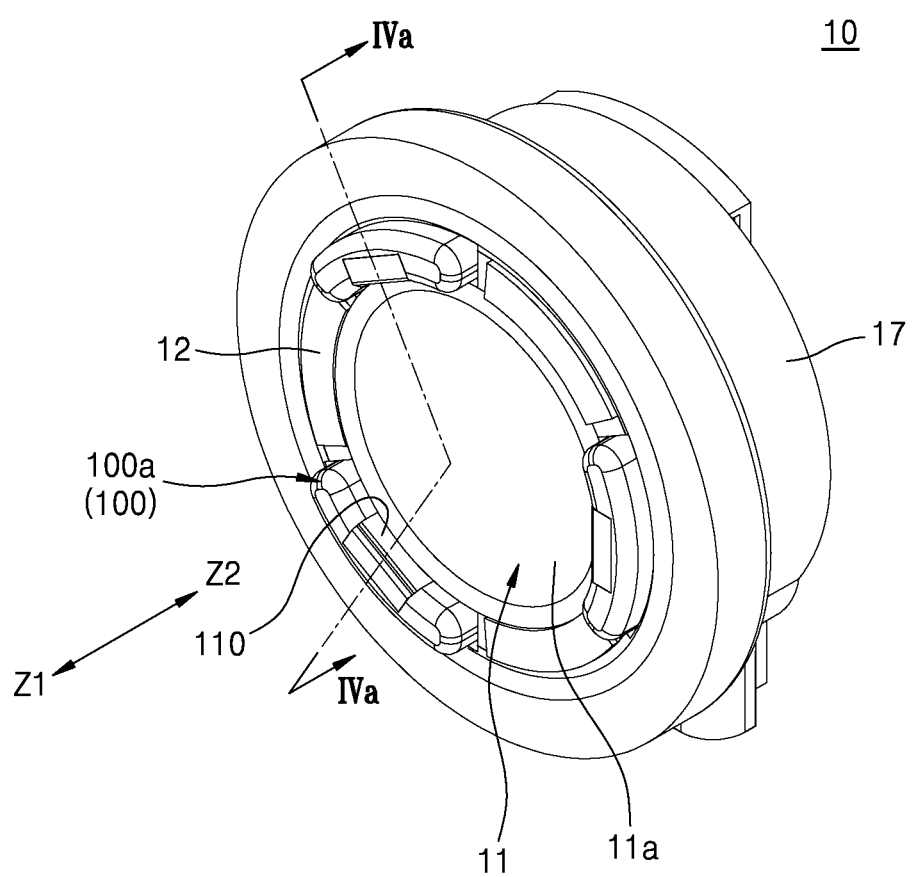
FIGS. 3A and 3B are assembled perspective views of the stethoscope head shown in FIG. 2, FIG. 3A showing a state in which a moving member is separated from an object, and FIG. 3B showing a state in which the moving member is in contact with and pressing the object.
Figure 3B:
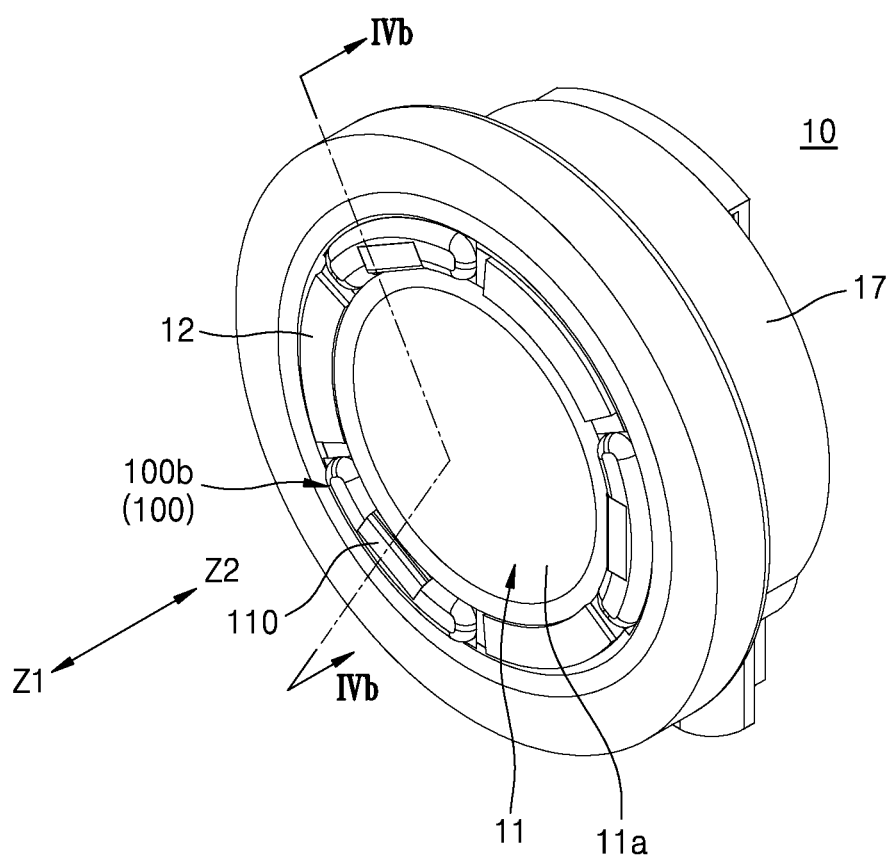
Figure 4A:
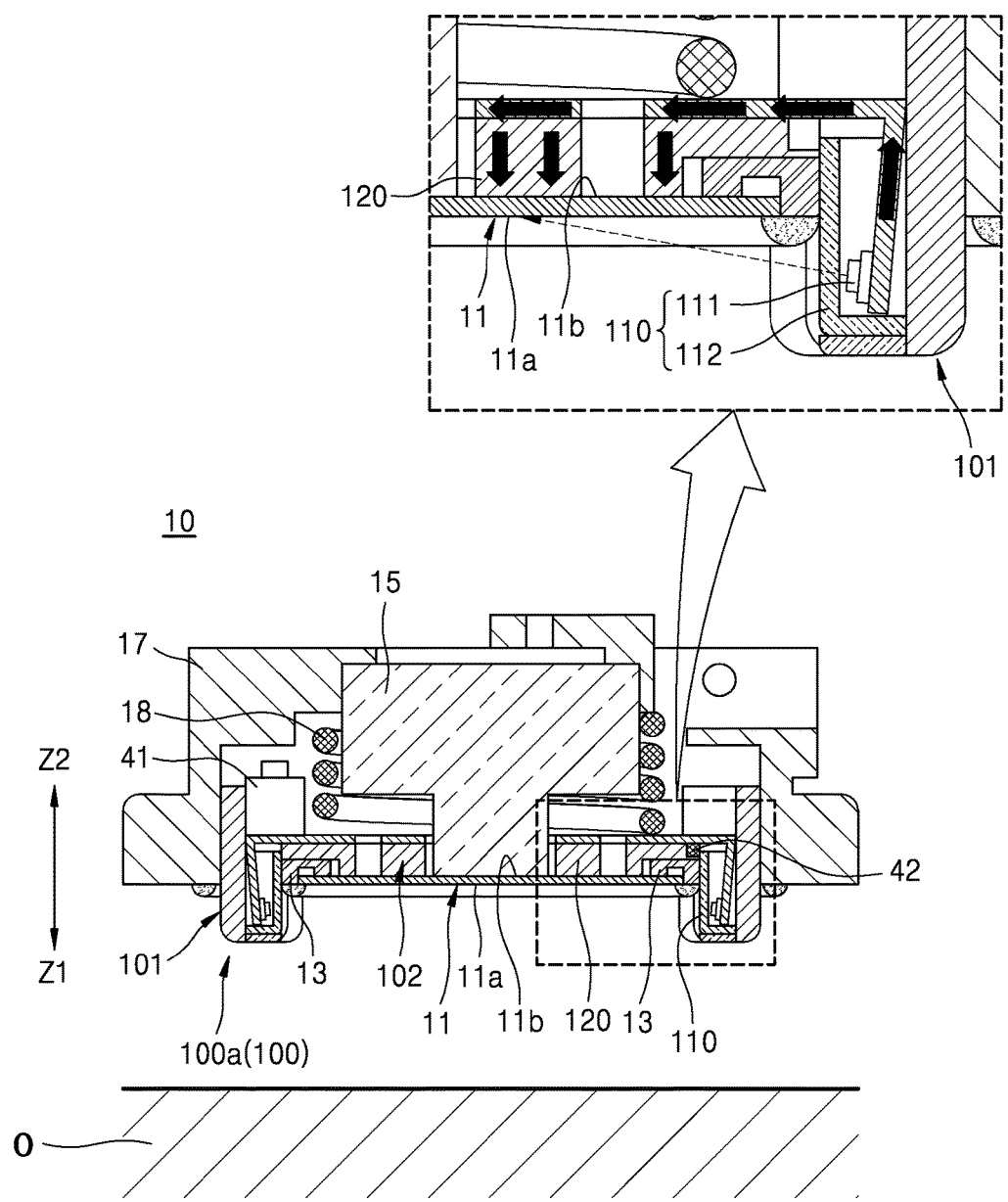
FIGS. 4A and 4B are cross-sectional views cut along cutting lines of FIGS. 3A and 3B.
Figure 4B:
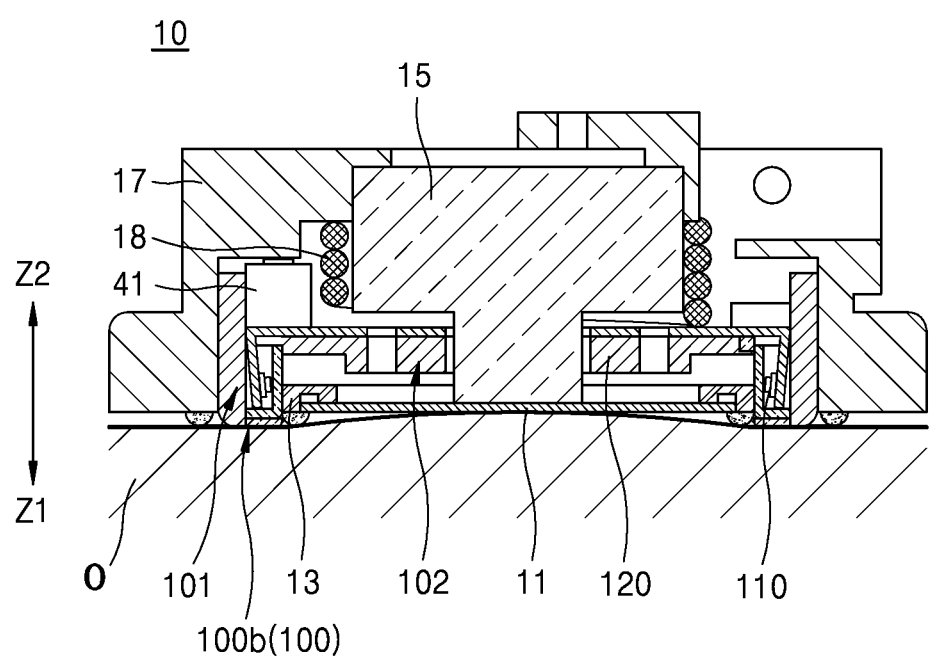
Figure 5:
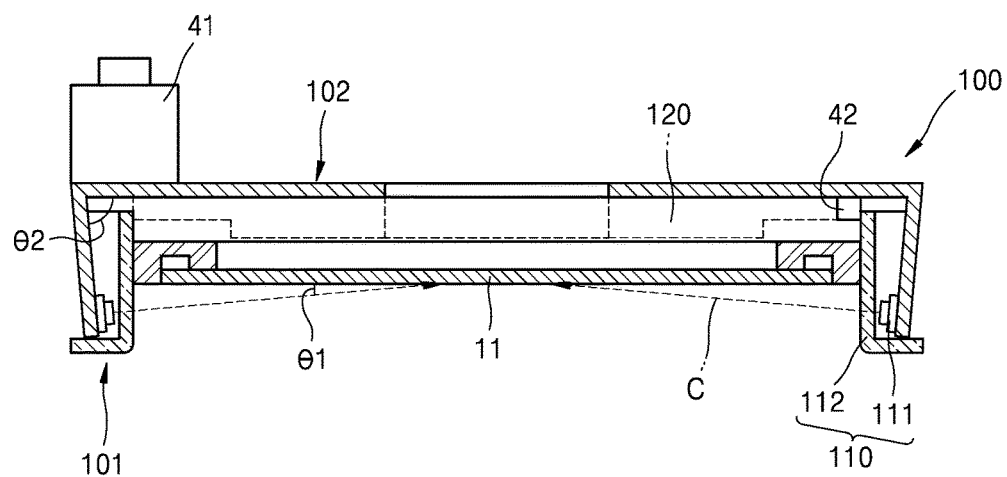
FIG. 5 is a cross-sectional view of the moving member including a light source, which is shown in FIG. 4A.

FIGS. 3A and 3B are assembled perspective views of the stethoscope head 10 shown in FIG. 2, FIG. 3A showing a state in which the moving member 100 is separated from the object O, and FIG. 3B showing a state in which the moving member 100 is in contact with and pressing the object O. FIGS. 4A and 4B are cross-sectional views cut along cutting lines of FIGS. 3A and 3B. FIG. 5 is a cross-sectional view of the moving member 100 including the light source 110, which is shown in FIG. 4A.

Referring to FIGS. 3A and 4A, along with separation of the stethoscope head 10 from the object O, a position of the moving member 100 moves in the first direction Z1 by the elastic member 18. Along with the movement of the position of the moving member 100 in the first direction Z1, the light source 110 is located at a position protruding in the first direction Z1 than the front surface 11a of the auscultatory sound receiver 11, and the heating source 120 is in contact with the rear surface 11b of the auscultatory sound receiver 11. In this case, the position of the moving member 100 is referred to as a first position 100a.

When the moving member 100 located at the first position 100a, the light source 110 emits ultraviolet rays on the front surface 11a of the auscultatory sound receiver 11. The front surface 11a of the auscultatory sound receiver 11 is a surface facing the object O and is in contact with the object O when an auscultatory sound is received from the object O. Therefore, the front surface 11a of the auscultatory sound receiver 11 is more easily exposed to various kinds of viruses than the other surfaces of the auscultatory sound receiver 11. According to the present embodiment, since the light source 110 emits ultraviolet rays on the front surface 11a of the auscultatory sound receiver 11, the front surface 11a of the auscultatory sound receiver 11, which is relatively weak at viruses, may be efficiently sterilized.

Referring to FIG. 5, the light source 110 may include a light-emitting diode 111 configured to emit ultraviolet rays and a lens 112 configured to spread light emitted by the light-emitting diode 111. The light source 110 may be disposed such that an angle θ1 between a center direction c of the emission of the ultraviolet rays and the auscultatory sound receiver 11 is an acute angle. For example, an extension angle θ2 of the protrusion region 101 of the moving member 100, in which the light source 110 is disposed, may be an acute angle with respect to the contact region 102 of the moving member 100. Since the center direction c of the emission of the ultraviolet rays makes an acute angle with respect to the auscultatory sound receiver 11, the ultraviolet rays may be concentrated on the auscultatory sound receiver 11, and non-intentional emission of the ultraviolet rays on a configuration other than the auscultatory sound receiver 11 or on the object O may be prevented.

Referring back to FIGS. 3A and 4A, when the moving member 100 located at the first position 100a, the heating source 120 is in contact with the rear surface 11b of the auscultatory sound receiver 11. The heating source 120 in contact with the rear surface 11b of the auscultatory sound receiver 11 conductively heats the auscultatory sound receiver 11.

The heating source 120 may be equipped with the light source 110. The heating source 120 may include a thermal conductive member such that the heating source 120 receives heat from the equipped light source 110. Therefore, the heating source 120 may receive heat generated by the light source 110 when the light source 110 emits ultraviolet rays. The thermal conductive member may include a metal, for example, aluminum (Al) or copper (Cu), but is not necessarily limited thereto. In addition, the heating source 120 may have various additional functions. For example, the heating source 120 may further include a metal printed circuit board (PCB) configured to apply a signal to the light source 110.

When the heating source 120 which has received heat from the light source 110 is in contact with the auscultatory sound receiver 11, the heat generated by the light source 110 may be transferred to the auscultatory sound receiver 11 through the heating source 120. Accordingly, the auscultatory sound receiver 11 may be pre-heated.

When energy, e.g., electric power, is applied to the light source 110 to emit ultraviolet rays, energy actually used to emit the ultraviolet rays in the light source 110 is merely a portion of the applied energy, and the other energy is discharged as heat. For example, only about 20% of the energy applied to the light source 110 is used to emit the ultraviolet rays, and about 80% of the applied energy may be discharged as heat. As described above, heat is generated when the light source 110 emits ultraviolet rays, and in the present embodiment, this heat is used to pre-heat the auscultatory sound receiver 11, and thus a separate heat source and energy for pre-heating may not be added. Accordingly, a structure for pre-heating may be simplified, and energy efficiency may be improved.

Referring to FIGS. 3B and 4B, when the user desires to auscultate through the stethoscope head 10, the user may make the stethoscope head 10 be in contact with the object O. When making the stethoscope head 10 be in contact with the object O, the moving member 100 is in contact with the object O. In this state, when the user pushes the stethoscope head 10 towards the object O, the moving member 100 moves in the second direction Z2.

Along with the movement of the moving member 100 in the second direction Z2, the light source 100 included in the protruding region 101 of the moving member 100 moves in the second direction Z2 from the first position 100a, and the heating source 120 included in the contact region 102 is separated from the rear surface 11b of the auscultatory sound receiver 11. In this case, the position of the moving member 100 is referred to as a second position 100b.

When the light source 110 moves back in the second direction Z2, normal auscultation by the auscultatory sound receiver 11 is possible.

If a structure in which the light source 110 is fixed to a position protruding in the first direction Z1 is used, the auscultatory sound receiver 11 cannot be in contact with the object O due to the protruding light source 110. Therefore, a normal auscultatory sound cannot be received by the auscultatory sound receiver 11. However, in the present embodiment, since the light source 110 moves back in the second direction Z2 during auscultation so as not to interrupt contact between the auscultatory sound receiver 11 and the object O, a normal auscultatory sound can be received by the auscultatory sound receiver 11.

In addition, when the moving member 100 is located at the second position 100b, the heating source 120 is separated from the rear surface 11b of the auscultatory sound receiver 11. Along with the separation of the heating source 120 from the rear surface 11b of the auscultatory sound receiver 11, the conductive heating of the auscultatory sound receiver 11 stops. Accordingly, the pre-heating of the auscultatory sound receiver 11 may stop.

Furthermore, since the auscultatory sound receiver 11 is separated from the heating source 120, an auscultatory sound may be smoothly received. If the auscultatory sound receiver 11 and the heating source 120 are in a contact state, when the auscultatory sound receiver 11 receives an auscultatory sound, the contact region 102 in which the auscultatory sound receiver 11 is in contact with the heating source 120 cannot vibrate, and accordingly, reception of a high-frequency band may be restricted. However, in the present embodiment, since a structure in which the auscultatory sound receiver 11 is separated from the heating source 120 when the moving member 100 is located at the second position 100b is used, reception of a high-frequency band is not restricted.

As described above, in the present embodiment, according to whether the stethoscope head 10 is in contact with the object O, the moving member 100 including the light source 110 and the heating source 120 is located at the first position 100a or the second position 100b, and thus pre-heating and sterilization in addition to auscultation are possible without attaching/detaching a separate device for the pre-heating and the sterilization.

Figure 6:
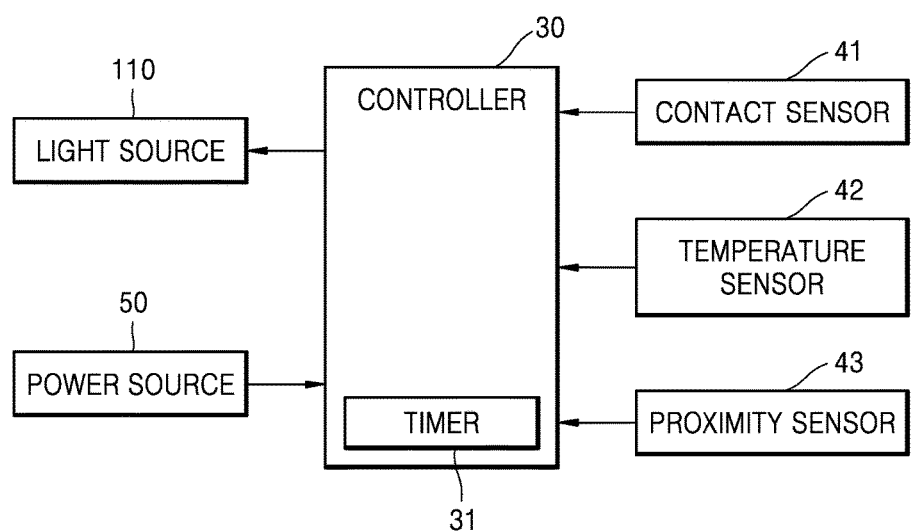
FIG. 6 is a block diagram for describing an operation of the light source of the stethoscope head, according to the present invention.

FIG. 6 is a block diagram for describing an operation of the light source 110 of the stethoscope head 10, according to the present invention. Referring to FIG. 6, the stethoscope head 10 may include a controller 30 for performing functions according to usages. The controller 30 may be connected to a power source 50 for supplying power to the light source 110.

The controller 30 may operate the light source 110 or stop the operation of the light source 110 according to whether a predetermined condition is satisfied even without receiving a separate input for pre-heating and sterilization from the user.

According to an embodiment, the controller 30 may control an operation of the light source 110 based on a contact sensor 41 configured to determine pressing according to movement of the moving member 100.

For example, the contact sensor 41 may be disposed on the rear surface of the moving member 100. The contact sensor 41 may not be pressed when the moving member 100 is located at the first position 100a as shown in FIG. 4A and may be pressed when the moving member 100 is located at the second position 100b as shown in FIG. 4B.

The controller 30 may stop an operation of the light source 110 when the contact sensor 41 is pressed and may operate the light source 110 when the pressing of the contact sensor 41 is released. Along with the stop of the operation of the light source 110, the sterilization and the pre-heating of the auscultatory sound receiver 11 stop, and along with the operation of the light source 110, the sterilization and the pre-heating of the auscultatory sound receiver 11 are performed.

As described above, only with an operation of the user who makes the stethoscope head 10 be in contact with the object O or separates the stethoscope head 10 from the object O, the contact sensor 41 may be pressed or released from the pressing, thereby determining whether the light source 110 operates. Accordingly, even without a separate operation of the user to start or stop sterilization and pre-heating, the sterilization and the pre-heating of the auscultatory sound receiver 11 may stop or start only with an operation of making the stethoscope head 10 be in contact with the object O or separating the stethoscope head 10 from the object O.

According to another embodiment, the controller 30 may control an operation of the light source 110 based on a temperature sensor 42 for detecting a temperature of the heating source 120. The temperature sensor 42 may be included in the moving member 100.

For example, when a temperature detected by the temperature sensor 42 is lower than a predetermined target temperature, the light source 110 may be operated, and when the temperature detected by the temperature sensor 42 is higher than or equal to the predetermined target temperature, the light source 110 may not be operated. Accordingly, the stethoscope head 10 performs sterilization and pre-heating until a temperature of the heating source 120 meets the predetermined target temperature but stops the sterilization and the pre-heating when the temperature of the heating source 120 meets the predetermined target temperature.

According to another embodiment, the controller 30 may control an operation of the light source 110 based on a proximity sensor 43 for detecting an approach of an external object to the light source 110. Herein, the external object is an object outside the stethoscope head 10, for example, the object O or the user.

Figure 7:
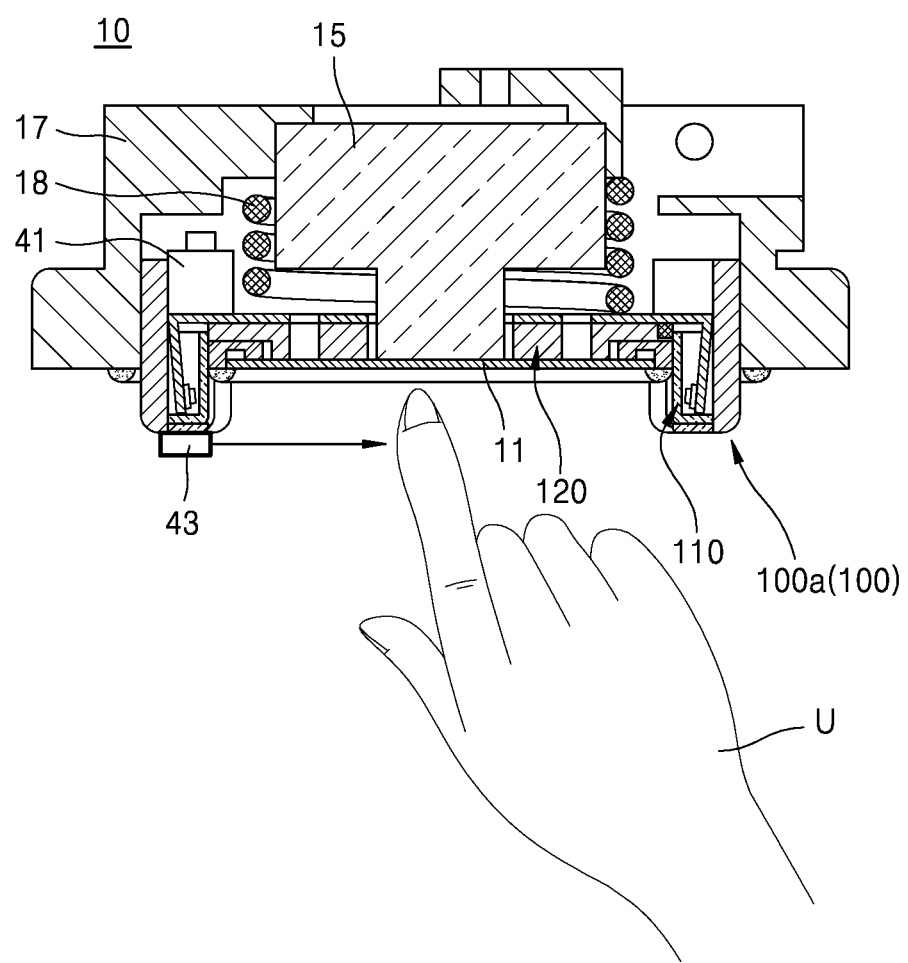
FIG. 7 illustrates an operating state of the stethoscope head including a proximity sensor, according to another embodiment of the present invention.

FIG. 7 illustrates an operating state of the stethoscope head 10 including the proximity sensor 43, according to another embodiment of the present invention. Referring to FIG. 7, the proximity sensor 43 may be disposed at the front of the stethoscope head 10. The proximity sensor 43 detects an approach of an external object U to the light source 110. When an approach of the external object U is detected by the proximity sensor 43, an operation of the light source 110 may stop. Accordingly, the external object U may be prevented from being exposed to the ultraviolet rays emitted from the light source 110.

According to another embodiment, the controller 30 may control an operation of the light source 110 based on a timer 31. The timer 31 may be used to set an operation time of the light source 110 required for sterilization and pre-heating.

The operation time of the light source 110 may be determined by taking into account at least one of power applied to the light source 110, a virus type, a degree of sterilization of the auscultatory sound receiver 11, and a pre-heating temperature of the auscultatory sound receiver 11. For example, when the power applied to the light source 110 is 0.125 W, a virus desired to be removed is influenza, and a required pre-heating temperature is 34° C., the operation time of the light source 110 may be about 211 seconds.

The controller 30 may control an operation of the light source 110 by comparing the operation time set to the light source 110 with an actual operation time of the light source 110.

Figure 8:
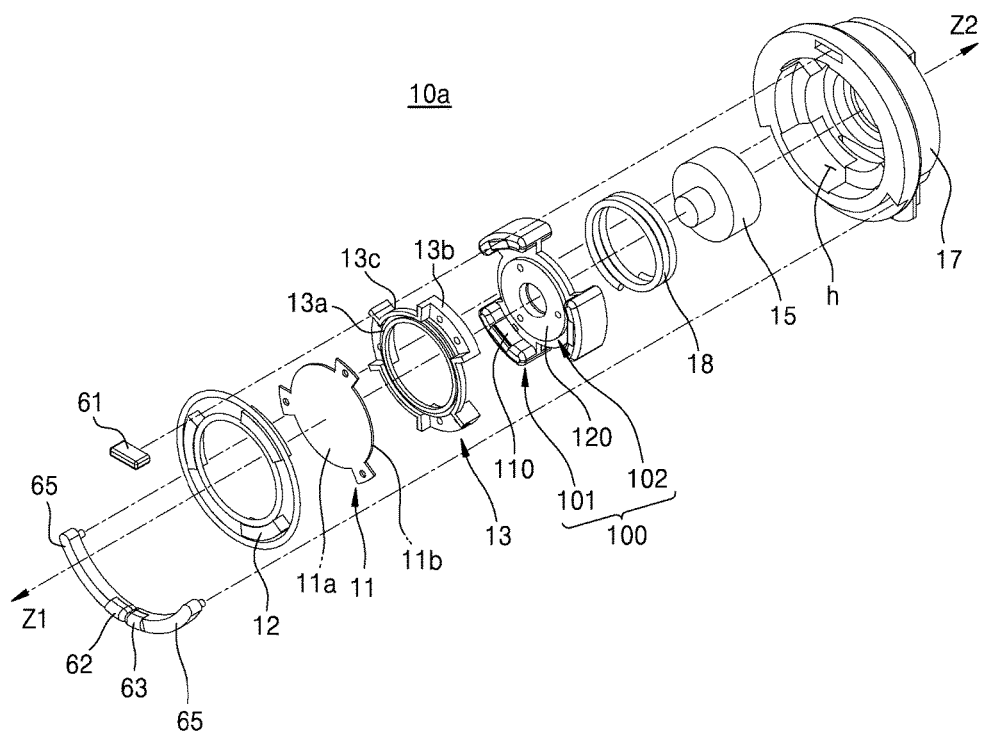
FIG. 8 is an exploded perspective view of a stethoscope head according to another embodiment of the present invention.

FIG. 8 is an exploded perspective view of a stethoscope head 10a according to another embodiment of the present invention. Referring to FIG. 8, the stethoscope head 10a further includes a plurality of electrocardiogram (ECG) electrodes 61, 62, and 63 for measuring an ECG of the object O besides the auscultatory sound receiver 11, the support member 13, the microphone 15, the head case 17, and the moving member 100.

Like components in the embodiments described above use like reference numerals, and a description thereof is omitted. Hereinafter, differences from the embodiments described above are mainly described.

The plurality of ECG electrodes 61, 62, and 63 are to measure an ECG of the object O and are in contact with different regions of the object O. Accordingly, the plurality of ECG electrodes 61, 62, and 63 measure voltages in a plurality of regions of the object O. An ECG of the object O may be measured by using measured potential differences between the ECG electrodes 61, 62, and 63.

The plurality of ECG electrodes 61, 62, and 63 may be arranged in the stethoscope case 17. A position of at least one of the plurality of ECG electrodes 61, 62, and 63 may move.

For example, positions of the two ECG electrodes 62 and 63 of the three ECG electrodes 61, 62, and 63 may move. A position of a first ECG electrode 61 is fixed, and positions of a second ECG electrode 62 and a third ECG electrode 63 may move by a rotary part 65.

The plurality of ECG electrodes 61, 62, and 63 may have a measurement position at which an ECG is measured from the object O and a standby position at which an ECG is not measured from the object O.

Along with the movement of the position of the at least one of the ECG electrodes 61, 62, and 63, separation distances between the ECG electrodes 61, 62, and 63 at the measurement position may differ from separation distances between the ECG electrodes 61, 62, and 63 at the standby position.

Figure 9A:
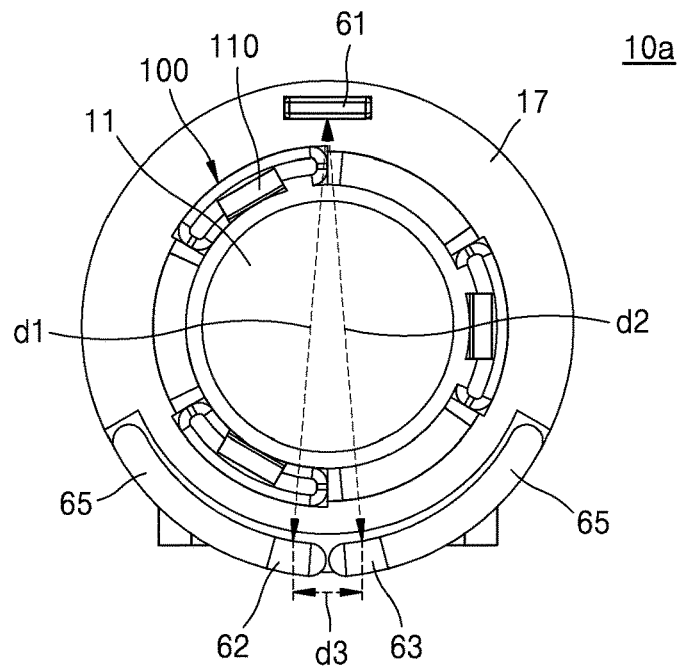
FIG. 9A illustrates a figure of the stethoscope head when electrocardiogram (ECG) electrodes of FIG. 8 are located at a standby position.
Figure 9B:
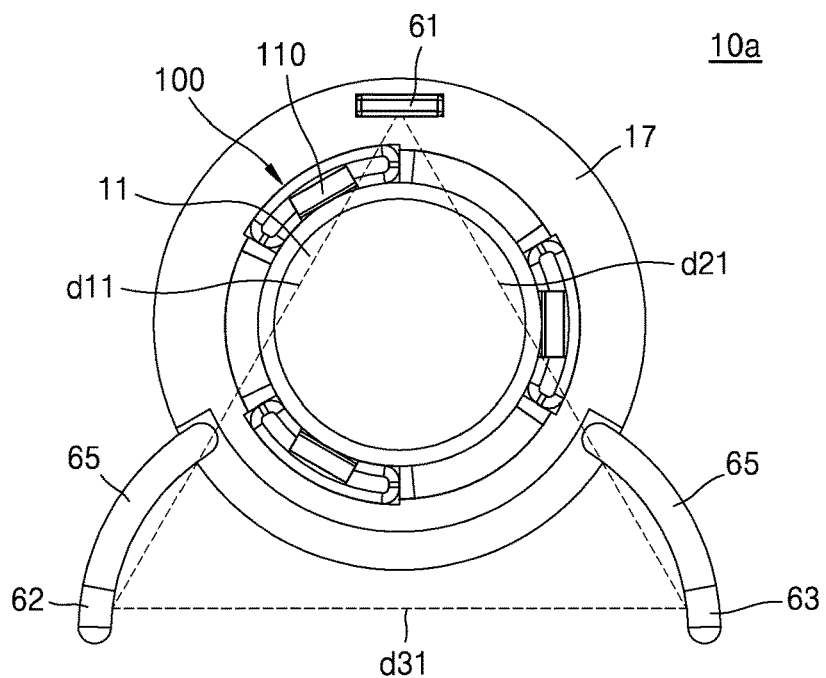
FIG. 9B illustrates a figure of the stethoscope head when the ECG electrodes of FIG. 8 are located at a measurement position.

FIG. 9A illustrates a figure of the stethoscope head 10a when the ECG electrodes 61, 62, and 63 of FIG. 8 are located at the standby position, and FIG. 9B illustrates a figure of the stethoscope head 10a when the ECG electrodes 61, 62, and 63 of FIG. 8 are located at the measurement position.

Referring to FIG. 9A, when an ECG is not measured from the object O, the plurality of ECG electrodes 61, 62, and 63 are located at the standby position. The plurality of ECG electrodes 61, 62, and 63 may be arranged so as not to overlap the head case 17. In this case, a distance between the first ECG electrode 61 and the second ECG electrode 62 may be d1, a distance between the first ECG electrode 61 and the third ECG electrode 63 may be d2, and a distance between the second ECG electrode 62 and the third ECG electrode 63 may be d3.

Referring to FIG. 9B, when the user desires to the ECG electrodes 61, 62, and 63 in the stethoscope head 10a, the user may move positions of the second and third ECG electrodes 62 and 63. For example, the second and third ECG electrodes 62 and 63 may be rotated by a predetermined angle by the rotary part 65.

Accordingly, the plurality of ECG electrodes 61, 62, and 63 are located at the measurement position. The second and third ECG electrodes 62 and 63 may not overlap the head case 17. In this case, a distance between the first ECG electrode 61 and the second ECG electrode 62 may be d11, a distance between the first ECG electrode 61 and the third ECG electrode 63 may be d21, and a distance between the second ECG electrode 62 and the third ECG electrode 63 may be d31.

As described above, by moving the second and third ECG electrodes 62 and 63, distances between the ECG electrodes 61, 62, and 63 may be adjusted. For example, all of the distances d1, d2, and d3 between the ECG electrodes 61, 62, and 63 before moving the ECG electrodes 61, 62, and 63 may be less than 4 Cm. All of the distances d11, d21, and d31 between the ECG electrodes 61, 62, and 63 after moving the ECG electrodes 61, 62, and 63 may be 4 Cm or more.

As described above, along with the movement of the at least two ECG electrodes 62 and 63 among the ECG electrodes 61, 62, and 63, separation distances between the ECG electrodes 61, 62, and 63 may be sufficiently secured when the ECG electrodes 61, 62, and 63 are used to measure an ECG, while setting the separation distances between the ECG electrodes 61, 62, and 63 to be less than in use when ECG electrodes 61, 62, and 63 are not used to measure an ECG. Accordingly, the ECG electrodes 61, 62, and 63 for measuring an ECG is easy to carry and can accurately measure an ECG.

Figure 10A:
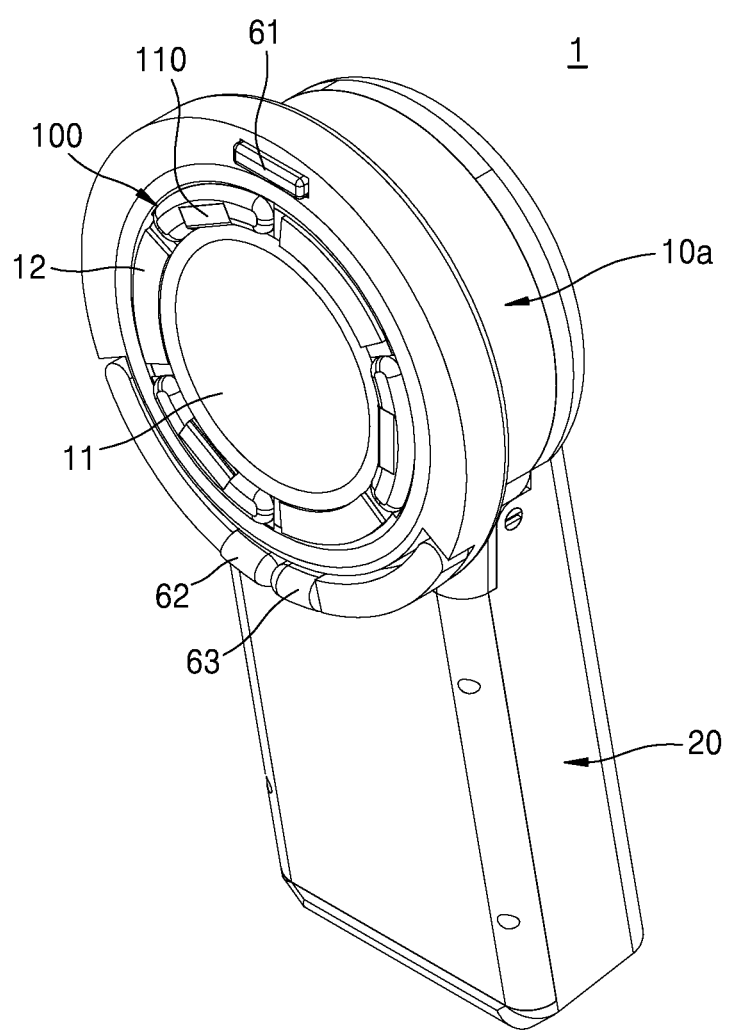
FIGS. 10A and 10B are a perspective view and an exploded perspective view for describing the stethoscope apparatus including the stethoscope head according to an embodiment of the present invention.
Figure 10B:
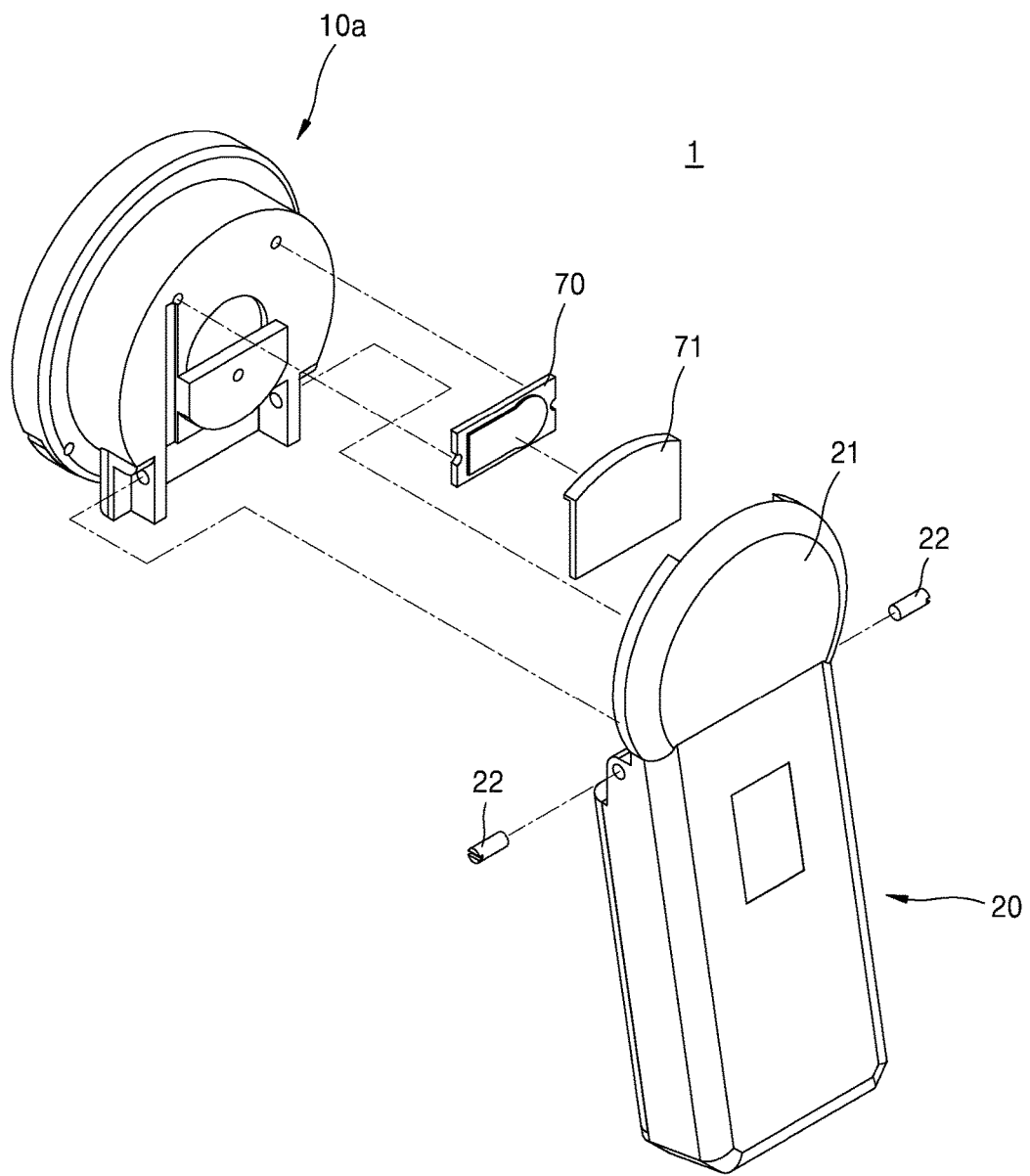

FIGS. 10A and 10B are a perspective view and an exploded perspective view for describing the stethoscope apparatus 1 including the stethoscope head 10a according to an embodiment of the present invention. FIG. 10A shows a state in which the stethoscope head 10a is assembled with the handle 20, and FIG. 10B shows a state in which the stethoscope head 10a is disassembled from the handle 20.

Referring to FIGS. 10A and 10B, the stethoscope apparatus 1 includes the stethoscope head 10a and the handle 20 which is a part for the user to grip the stethoscope head 10a.

The stethoscope head 10a includes the auscultatory sound receiver 11, the support member 13, the moving member 100, the microphone 15, and the head case 17 described above. A description of the same configuration as described with respect to the above-described embodiments is omitted. Hereinafter, the stethoscope head 10a and the handle 20 are mainly described.

The handle 20 may be movably connected to the stethoscope head 10a. For example, the handle 20 may be movably connected to the stethoscope head 10a around a rotary axis. A rotary shaft 22 may be disposed between the head case 17 and the handle 20.

The handle 20 includes a rotation restriction part 21 supporting the rear surface of the head case 17. Rotation of the head case 17 by a predetermined angle or more may be restricted by the rotation restriction part 21.

A pressure detector 70 detects a pressure of the handle 20 on the stethoscope head 10a. The pressure detector 70 may be disposed between the stethoscope head 10a and the handle 20. For example, the pressure detector 70 may be disposed between the head case 17 of the stethoscope head 10a and the rotation restriction part 21 of the handle 20.

The user may get a pressure applied between the object O and the stethoscope head 10a based on pressure information detected by the pressure detector 70. Accordingly, the user may adjust a force to be applied to the handle 20 such that the pressure of the stethoscope head 10a on the object O is an appropriate pressure.

An elastic member 71 may be disposed between the pressure detector 70 and the rotation restriction part 21. The pressure detector 70 may accurately detect a pressure applied by the rotation restriction part 21 by being in surface contact with the rotation restriction part 21 through the elastic member 71. An example of a material of the elastic member 71 is a rubber material.

Figure 11:
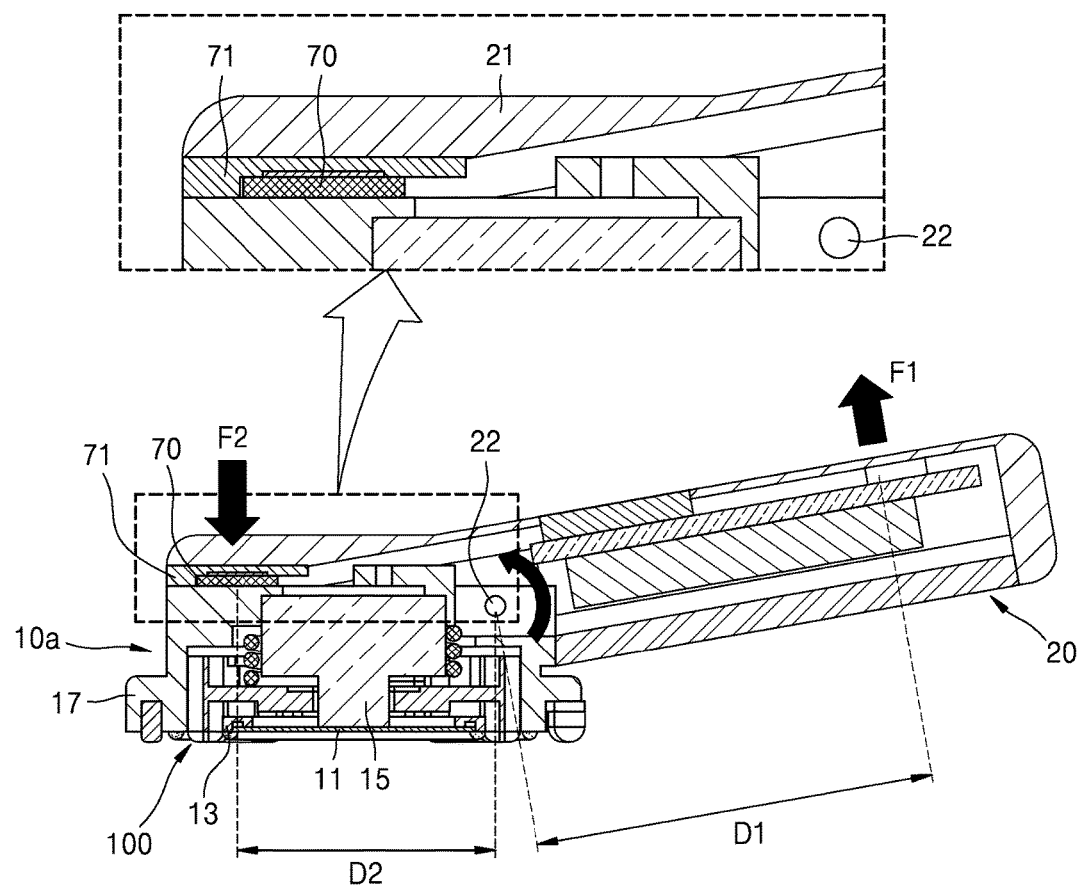
FIG. 11 is a schematic cross-sectional view for describing a use state of the stethoscope apparatus according to an embodiment of the present invention.

FIG. 11 is a schematic cross-sectional view for describing a use state of the stethoscope apparatus 1 of FIG. 10A.

Referring to FIG. 11, the user may make the stethoscope head 10a be in contact with the object O in a state of gripping the handle 20. The user may press the handle 20 of the stethoscope apparatus 1 such that the stethoscope head 10a faces the object O, in a state of making the stethoscope head 10a be in contact with the object O.

Along with the pressing the handle 20 of the stethoscope apparatus 1, the pressure detector 70 disposed between the handle 20 and the head case 17 is pressed by a predetermined force. For example, when the user presses a pressing point of the handle 20 by a first force F1, the pressure detector 70 is pressed by a second force F2 based on the principle of the lever. Accordingly, the stethoscope head 10a presses the object O by a force corresponding to the second force F2.

A distance D1 between the pressing point and the rotary shaft 22 may differ from a distance D2 between the pressure detector 70 and the rotary shaft 22. Accordingly, the first force F1 applied to the pressing point may differ from the second force F2 applied to the pressure detector 70. For example, when the distance D1 between the pressing point and the rotary shaft 22 may is greater than the distance D2 between the pressure detector 70 and the rotary shaft 22, the first force F1 applied to the pressing point may be less than the second force F2 applied to the pressure detector 70. When the distance D1 between the pressing point and the rotary shaft 22 may is less than the distance D2 between the pressure detector 70 and the rotary shaft 22, the first force F1 applied to the pressing point may be greater than the second force F2 applied to the pressure detector 70.

Therefore, the user may easily press the head case 17 by an appropriate pressure by adjusting a position of the pressing point at which a force is applied to the handle 20 or a magnitude of the force F1 to be applied to the handle 20. In addition, amplification of noise may be reduced by increasing a voltage range detectable by the pressure detector 70.

Figure 12:
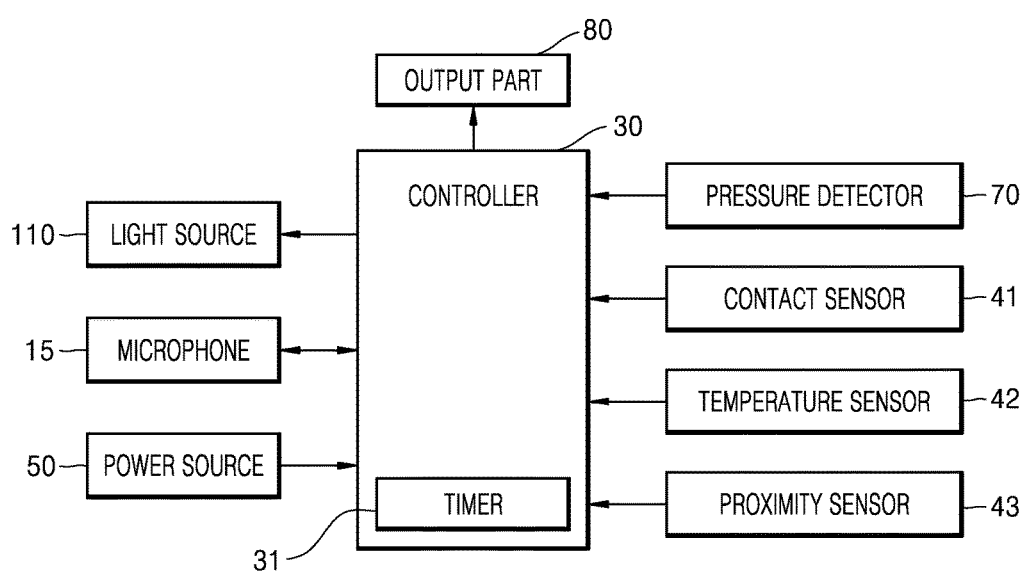
FIG. 12 is a block diagram for describing an operation of the stethoscope apparatus, according to the present invention.

FIG. 12 is a block diagram for describing an operation of the stethoscope apparatus 1, according to the present invention. Referring to FIG. 12, the stethoscope apparatus 1 may include the controller 30 for performing functions according to usages. The controller 30 may be connected to the power source 50 for supplying power to the microphone 15.

According to an embodiment, the controller 30 may control the microphone 15 based on information detected by the pressure detector 70. For example, the controller 30 may operate the microphone 15 only when detected pressure information satisfies an appropriate pressure. That is, when the detected pressure information does not satisfy the appropriate pressure, the microphone 15 may not be operated. Accordingly, when a pressure between the stethoscope head 10 and the object O does not satisfy the appropriate pressure, an inflow of friction and peripheral noise through the microphone 15 may be prevented.

According to another embodiment, the controller 30 may control the light source 110 based on at least one of the contact sensor 41, the temperature sensor 42, and the proximity sensor 43. A description of the present embodiment has been described with reference to FIG. 6, and thus the description of the present embodiment is omitted herein.

According to another embodiment, the controller 30 may provide information detected by the various kinds of sensors 41, 42, and 43 and the pressure detector 70 to the user through an output part 80. The output part 80 may include at least one of a display for providing image information and a speaker for providing acoustic information.

For example, the controller 30 may provide whether pressure information detected by the pressure detector 70 satisfies the appropriate pressure, is less than the appropriate pressure, or is greater than the appropriate pressure to the user through the output part 80 by at least one of a visual method and an acoustic method. As an example of the visual method, the output part 80 may output a different color according to whether detected pressure information satisfies the appropriate pressure, is less than the appropriate pressure, or is greater than the appropriate pressure. As an example of the acoustic method, the output part 80 may output a different alarm sound according to whether detected pressure information satisfies the appropriate pressure, is less than the appropriate pressure, or is greater than the appropriate pressure.

As another example, the controller 30 may provide information about the object O, which has been received through the microphone 15, to the user through the output part 80. For example, the output part 80 may output the number of heartbeats of the object O by means of a numeric value or a graph. For example, the output part 80 may output whether a status of the object O is normal or abnormal.

As another example, the controller 30 may provide information about a state of the stethoscope head 10 to the user through the output part 80. For example, the output part 80 may output whether the stethoscope head 10 is during auscultation, during pre-heating and sterilization, or in a competed state of the pre-heating and the sterilization.

With respect to the embodiments described above, an example in which the moving member 100 of the stethoscope head 10 or 10a includes both the light source 110 and the heating source 120 has been mainly described. However, the configuration of the moving member 100 of the stethoscope head 10 or 10a is not limited thereto, and the moving member 100 of the stethoscope head 10 or 10a may include any one of the light source 110 and the heating source 120.

Figure 13A:
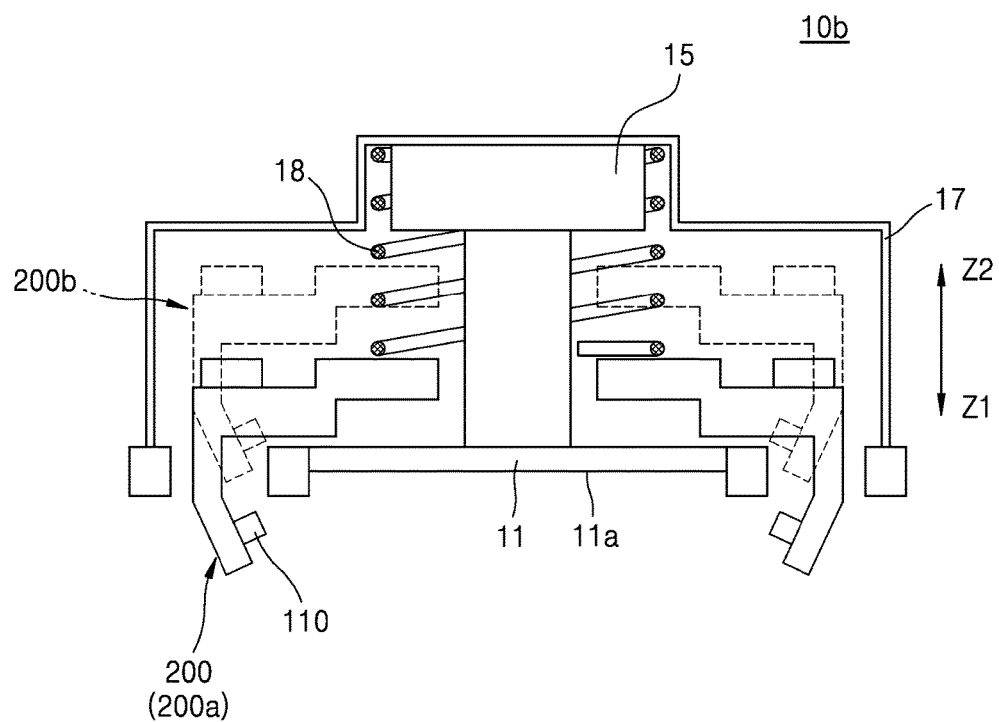
FIGS. 13A and 13B are schematic cross-sectional views of a stethoscope head according to another embodiment of the present invention.

According to an embodiment, as shown in FIG. 13A, a moving member 200 of a stethoscope head 10b may include the light source 110 and may not include the heating source 120. In this case, when the moving member 200 is located at a first position 200a, the light source 110 protrudes than the front surface 11a of the auscultatory sound receiver 11, but the moving member 200 may not be in contact with the auscultatory sound receiver 11. During auscultation, the moving member 200 moves in the second direction Z2 and is located at a second position 200b, and accordingly, contact between the auscultatory sound receiver 11 and the object O may not be disturbed due to the light source 110.

Figure 13B:
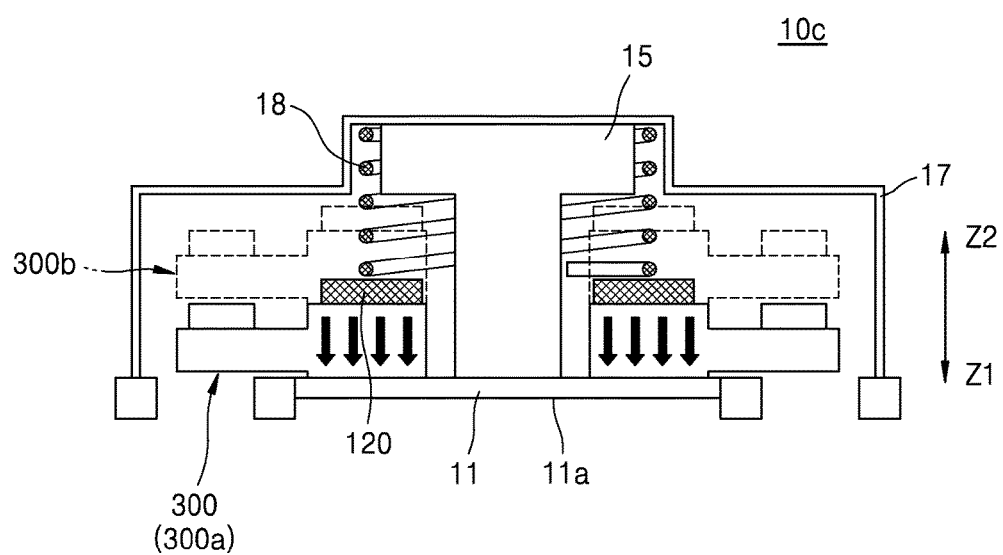

According to another embodiment, as shown in FIG. 13B, a moving member 300 of a stethoscope head 10c may include the heating source 120 and may not include the light source 110. In this case, unlike the embodiments described above, the heating source 120 may generate heat independently from the light source 110. In this case, when the moving member 300 is located at a first position 300a, the moving member 300 is in contact with the auscultatory sound receiver 11 but does not protrude in the first direction Z1 than the front surface 11a of the auscultatory sound receiver 11. When the moving member 300 is in contact with the auscultatory sound receiver 11, heat generated by the heating source 120 is transferred to the auscultatory sound receiver 11 through the moving member 300 such that the auscultatory sound receiver 11 is heated. During auscultation, the moving member 300 moves in the second direction Z2 and is located at a second position 300b, and accordingly, the auscultatory sound receiver 11 is separated from the moving member 300, and conductive heating by the heating source 120 may stop.

While the present invention has been particularly shown and described with reference to exemplary embodiments thereof, it will be understood by those of ordinary skill in the art that various changes in form and details may be made therein without departing from the spirit and scope of the present invention as defined by the following claims.

The use of the term "said" or a similar directional term in the specification (in particular, in claims) of the invention may correspond to both the singular and the plural. In addition, when a range is disclosed, individual values belonging to the range are included (if there is no disclosure opposed to this), and this is the same as if each of the individual values forming the range is disclosed in the detailed description of the invention. Finally, for steps forming the methods according to the present invention, if an order is not clearly disclosed or, if there is no disclosure opposed to the clear order, the steps can be performed in any order deemed proper. The present invention is not necessarily limited to the disclosed order of the steps. The use of all illustrations or illustrative terms (for example, and so forth, etc.) is simply to describe the present invention in detail, and the scope of the present invention is not limited due to the illustrations or illustrative terms unless they are limited by claims. In addition, it will be understood by those of ordinary skill in the art that various modifications, combinations, and changes can be formed according to design conditions and factors without departure from the scope and idea of the present invention.

The invention claimed is:

1. A stethoscope head comprising:
an auscultatory sound receiver configured to receive an auscultatory sound from an object;
a support member configured to support at least a part of the auscultatory sound receiver; and
a moving member comprising a light source configured to emit ultraviolet rays for sterilization to the auscultatory sound receiver, and capable of moving a position thereof in a first direction orienting to the object and a second direction opposite to the first direction,
wherein the moving member comprises a protruding region which protrudes outside of the auscultatory sound receiver in the first direction when the auscultatory sound receiver does not contact the object.

2. The stethoscope head of claim 1, wherein, when the stethoscope head is in contact with the object, the moving member moves in the second direction, and when the stethoscope head is away from the object, the moving member moves in the first direction, and
wherein the moving member is movable between a first position in which the protruding region having the light source protrudes outside of the auscultatory sound receiver in the first direction and a second position which is apart in the second direction from the first position so as not to interfere with contact between the auscultatory sound receiver and the object, and
wherein, when the stethoscope head is in contact with the object, the protrusion region is pressed by the object and the moving member moves in the second direction to be the second position.

3. The stethoscope head of claim 2, wherein, when the moving member is located at the first position, the light source emits ultraviolet rays on the front surface of the auscultatory sound receiver, the front surface facing the object.

4. The stethoscope head of claim 3, wherein the light source is disposed such that a center direction of the emission of the ultraviolet rays makes an acute angle with the auscultatory sound receiver.

5. The stethoscope head of claim 2, wherein the moving member further comprises a heating source configured to heat the auscultatory sound receiver.

6. The stethoscope head of claim 5, wherein, when the moving member is located at the first position, the heating source is in contact with the auscultatory sound receiver.

7. The stethoscope head of claim 5, wherein,
when the moving member is located at the second position, the heating source is away from the auscultatory sound receiver.

8. The stethoscope head of claim 5, wherein the heating source is equipped with the light source and comprises a thermal conductive member.

9. The stethoscope head of claim 5, wherein the moving member further comprises a temperature sensor configured to measure a temperature of the heating source.

10. The stethoscope head of claim 2, wherein the stethoscope head further comprises a contact sensor configured to be pressed according to movement of the moving member.

11. The stethoscope head of claim 1, further comprising a plurality of electrocardiogram (ECG) electrodes configured to measure an ECG of the object,
wherein at least one of the plurality of ECG electrodes is movable.

12. The stethoscope head of claim 11, wherein the plurality of ECG electrodes have a measurement position at which an ECG is measured from the object and a standby position at which the ECG is not measured from the object.

13. The stethoscope head of claim 12, wherein
separation distances between the plurality of ECG electrodes when the plurality of ECG electrodes are located at the measurement position are greater than separation distances between the plurality of ECG electrodes when the plurality of ECG electrodes are located at the standby position.

14. A stethoscope apparatus comprising:
the stethoscope head of claim 1; and
a handle connected to the stethoscope head.

15. The stethoscope apparatus of claim 11, wherein the handle is rotatably connected to the stethoscope head.

16. The stethoscope apparatus of claim 12, further comprising a pressure detector configured to detect pressure of the handle on the stethoscope head.

17. The stethoscope apparatus of claim 11, wherein at least one of the stethoscope head and the handle further comprises an output part configured to provide information to a user.

18. A stethoscope head of comprising:
an auscultatory sound receiver configured to receive an auscultatory sound from an object;
a support member configured to support at least a part of the auscultatory sound receiver;
a moving member comprising a light source configured to emit ultraviolet rays for sterilization to the auscultatory sound receiver, and capable of moving a position thereof in a first direction orienting to the object and a second direction opposite to the first direction; and
a proximity sensor configured to detect an approach of an external object to the light source.

19. A stethoscope head comprising:
an auscultatory sound receiver configured to receive an auscultatory sound from an object;
a support member configured to support at least a part of the auscultatory sound receiver; and
a moving member comprising a heating source configured to heat the auscultatory sound receiver, and capable of moving a position thereof in a first direction orienting to the object and a second direction opposite to the first direction, wherein the moving member comprises a protruding region which protrudes outside of the auscultatory sound receiver in the first direction when the auscultatory sound receiver does not contact the object.

* * * * *